(12) United States Patent
Simchony et al.

(10) Patent No.: US 8,939,895 B2
(45) Date of Patent: Jan. 27, 2015

(54) SELF-CENTRALIZING INFLATABLE BALLOON

(75) Inventors: Tal Simchony, Hod Ha Sharon (IL); Ran Mendelewicz, Herzliya (IL); Yogev Yadid, Kadima (IL); Reuvan Eshel, Haifa (IL); Yoram Blum, Givat Shmuel (IL)

(73) Assignee: G. I. View Ltd., Ramat Gan (IL)

( * ) Notice: Subject to any disclaimer, the term of this patent is extended or adjusted under 35 U.S.C. 154(b) by 262 days.

(21) Appl. No.: 13/510,194

(22) PCT Filed: Nov. 17, 2010

(86) PCT No.: PCT/IL2010/000960
§ 371 (c)(1),
(2), (4) Date: Jul. 11, 2012

(87) PCT Pub. No.: WO2011/061740
PCT Pub. Date: May 26, 2011

(65) Prior Publication Data
US 2012/0283514 A1 Nov. 8, 2012

Related U.S. Application Data

(60) Provisional application No. 61/261,784, filed on Nov. 17, 2009.

(51) Int. Cl.
*A61B 1/00* (2006.01)
*A61B 1/015* (2006.01)
(Continued)

(52) U.S. Cl.
CPC ............. *A61B 1/015* (2013.01); *A61B 1/00082* (2013.01); *A61M 25/0122* (2013.01);
(Continued)

(58) Field of Classification Search
CPC .......... A61B 1/00082; A61M 25/1002; A61M 25/1025
USPC .................... 600/114–116; 604/95.03, 96.01, 604/101.01, 103, 103.03, 103.07
See application file for complete search history.

(56) References Cited

U.S. PATENT DOCUMENTS

| | | | | |
|---|---|---|---|---|
| 4,276,874 A | * | 7/1981 | Wolvek et al. | 600/18 |
| 4,295,464 A | * | 10/1981 | Shihata | 606/127 |
| 5,364,353 A | * | 11/1994 | Corfitsen et al. | 604/95.03 |
| 5,398,670 A | * | 3/1995 | Ortiz et al. | 600/114 |
| 5,968,012 A | | 10/1999 | Ren et al. | |
| 6,485,409 B1 | * | 11/2002 | Voloshin et al. | 600/115 |

(Continued)

FOREIGN PATENT DOCUMENTS

WO WO 2009/009472 1/2009

*Primary Examiner* — Matthew J Kasztejna
(74) *Attorney, Agent, or Firm* — Frommer Lawrence & Haug LLP; William S. Frommer (57) ABSTRACT

An apparatus is presented for use with a biologically-compatible-fluid pressure source. The apparatus comprises an elongated carrier defining a fluid passageway and adapted to be inserted through a proximal opening of a body lumen having a main axis and certain diameter; an inflatable balloon assembly having an inflatable part self-deformable between its substantially circular geometric state and multiple elongated geometry states in which cross sectional dimensions of the inflatable balloon part are different in accordance with the diameter of the lumen, and being in fluid communication with said fluid passageway, the cross sectional dimension of the substantially circular geometric state being equal to or greater than said diameter of said body lumen; and at least one sleeve extending from at least one end respectively of said inflatable part of the balloon assembly along a central axis of said inflatable balloon part, said at least one sleeve being by its one end is rigidly coupled to the respective end of the balloon part and having one of the following configurations: (a) being by its other end fixed to the carrier at a certain location and being foldable and extendable in accordance with longitudinal deformation of the inflatable balloon part, and (b) having a fixed length and being by its other end slidable along the carrier in accordance with longitudinal deformation of the inflatable balloon part. Deformation of the inflatable part of the balloon maintains the balloon assembly orientation such that the carrier passing through the balloon assembly substantially coincides with said main axis of said lumen.

18 Claims, 6 Drawing Sheets

(51) Int. Cl.
*A61M 25/01* (2006.01)
*A61M 25/10* (2013.01)
*A61M 25/00* (2006.01)

(52) U.S. Cl.
CPC ........... *A61M25/10* (2013.01); *A61M 25/1018* (2013.01); *A61B 1/00147* (2013.01); *A61M 25/0082* (2013.01); *A61M 2025/1068* (2013.01); *A61M 2025/1081* (2013.01)
USPC ........ 600/115; 600/114; 600/116; 604/95.03; 604/96.01; 604/101.01; 604/103.03; 604/103.07

(56) References Cited

U.S. PATENT DOCUMENTS

| | | | |
|---|---|---|---|
| 6,702,735 B2* | 3/2004 | Kelly | 600/115 |
| 6,733,439 B2* | 5/2004 | Zigler | 600/115 |
| 8,419,678 B2* | 4/2013 | Cabiri et al. | 604/99.01 |
| 8,556,851 B2* | 10/2013 | Hirszowicz et al. | 604/96.01 |
| 2004/0236366 A1 | 11/2004 | Kennedy, II et al. | |
| 2005/0038318 A1 | 2/2005 | Goldwasser | |
| 2009/0093801 A1 | 4/2009 | Crossman | |

* cited by examiner

SELF-CENTRALIZING INFLATABLE BALLOON

This application is filed pursuant to 35 USC 371 based on International Application number PCT/IL2010/000960, filed Nov. 17, 2010, which claims priority to U.S. provisional application No. 61/261,784, filed Nov. 17, 2009, the entirety of which is incorporated herein by reference.

FIELD OF THE INVENTION

This invention relates to the field of medical devices and, in particular, to inflatable balloons designed for being inserted into and travelling through body cavities.

BACKGROUND OF THE INVENTION

In many medical disciplines, thin and elongated carrier tubes carrying imaging devices are inserted into a patient's body to inspect areas of interest of the body for diagnostic purposes, or to aid medical personnel in chirurgical procedures. In the insertion and motion of the carrier within the body lumen, a control technique should be provided to ensure that the image capturing device's field of view (FOV) includes the region of interest, and does not veer from away from a desired orientation.

For example, in colonoscopy, an examination of body lumens, such as the colon and part of the small bowel, is performed with a CCD camera or a fiber optic camera on a flexible carrier passed through the anus. The examination may provide a visual diagnosis (e.g. ulceration, polyps) and grant the opportunity for biopsy or removal of suspected lesions. In colonoscopy, during at least a preliminary inspection sweep (i.e. a passage of the carrier throughout the length of a chosen lumen), the camera should be kept near the central axis of the inspected lumen and pointing forward. In this manner, the area of lumen walls in the camera's FOV is maximized, thereby increasing the accuracy of the inspection. The inspection time is also reduced, thereby reducing the patient's discomfort.

GENERAL DESCRIPTION

There is a need in the art in a novel technique for inspection of tissue inside a body cavity or body lumen with a medical device/tool. The present invention solves this need by providing a novel apparatus for navigating the inspection tool through the cavity, suitable for different cavity cross-sectional dimensions (e.g. diameter) or for a cavity having varying cross-section there along.

It should be understood that the principles of the configuration and operation of the apparatus of the present invention can be used with various applications requiring navigation through the cavity. More specifically the invention is used in endoscopy applications, especially colonoscopy, and is therefore described below with respect to this specific application. However, the invention should not be limited to this application. An apparatus of the invention, for use in a body lumen, comprises a carrier, adapted to be inserted through a proximal opening of a body lumen, and carrying an inflatable balloon and an imaging unit, while the latter might be replaced by any other medical tool in other applications. The invention is about the carrier with the inflatable balloon and a manner in which the balloon is self-orientable with regard to its geometry/deformation and position/orientation within the body cavity of a different/varying diameter.

The inflatable balloon of the present invention forms a sealing contact with the wall of the body lumen to enable a medical device to propel by rear pressure through a body lumen. The body lumen typically has a varying diameter throughout its length, as well as might be of a curvilinear shape, i.e. might include several corners, which must be navigated through. Therefore, the inflatable balloon is configured to be deformable in accordance with a change in the diameter of the body lumen portion in which it navigates (by adapting itself to match the cross sectional shape of the lumen via longitudinal folds), while continuously form a sealing contact with the inner walls of the body lumen. To this end, the inflatable balloon preferably has a maximal diameter larger than (or sometimes equal to) to the largest expected value of the lumen diameter through which the carrier is to travel. In some embodiments, the maximal diameter of the balloon in an undeformed state thereof is in the range of 70-90 millimeters for internal pressures in the range between about 10 and 60 millibars, in order to ensure that the balloon can provide a pressure seal in a lumen (such as the stomach) having a diameter varying between 20 and 80 millimeters.

In order to enable self adjustment (deformation) of the balloon's shape in response to a change in the lumen diameter, the balloon material and thickness are appropriately selected such that the balloon is practically not extendable but expandable. More specifically, when a stress force (tension) is applied to the balloon material, an extension of the material is very small, e.g. not exceeding 10% for 4-6 mPa. Accordingly, if the circular-shaped balloon enters a smaller diameter region of the lumen, a force is applied to the balloon from the walls of the lumen deforming the balloon towards its elongated, elliptical-like, shape while practically not causing extension of the material itself.

Furthermore, considering colonoscopy application, due to the significant difference between the diameters of the different parts forming the GI tract, the inflatable balloon of the present invention is configured and operable to reach a certain maximal diameter corresponding to the characteristic diameter of the regions of the lumen to be inspected, by controlling a pressure inside the balloon. In this connection, it should be noted that in order to enable propelling of the balloon through the body lumen, a certain pressure difference between the pressure inside the balloon and the rear pressure outside thereof (i.e. pressure applied to the external surface of the balloon while in the lumen) should be maintained (the pressure in the balloon should also be higher than said rear pressure outside thereof). The apparatus is configured such that the inflatable balloon performs self adjustment of its geometry and orientation during its propelling through the lumen in response to changes in the shape of lumen.

Thus, the balloon is deformable between its expanded state (substantially circular) and various folded states in which it has different elongated non-circular geometries. It should be understood that the desired orientation of the balloon in the lumen is such that a longitudinal (central) axis of the elongated-state balloon is substantially parallel to the axis of the lumen within the current region thereof where the balloon becomes located during the propagation. Considering medical applications, this requirement is to be satisfied in order to keep appropriate orientation of a medical device carried by the same carrier as the balloon. For example, such medical device may include an imaging unit.

Thus, the inflatable balloon responds to changes in the diameter of the lumen by self-inflation as the lumen diameter increases, and by self-deflation as the lumen diameter decreases, all while maintaining satisfactory contact with the lumen via an unfolding and collapsing of the balloon along the balloon's folds. All this occurs concurrently with controllable application of pressure to maintain the desired pressure difference as described above. To this end, the apparatus is associated with an appropriately preprogrammed control unit and a pressure source. The pressure difference is chosen to maintain an appropriate seal between the balloon and the lumen, without undue pressure on the lumen, and to avoid excessive friction with the lumen.

Moreover, considering such body lumens as the anus, the stomach, and other regions of the GI tract, they have highly mobile walls that tend to be easily displaced when acted on by a force. These walls are also highly muscular and expand and contract in various cycles. At any time, the lumen can be in an open or closed state, but most often is in a collapsed state. Therefore, the device of the present invention comprises a stabilizing element configured and operable to dilate the lumen to thereby create a working space within the lumen to facilitate the advancement of the apparatus, which in imaging applications also facilitates the imaging of the inner tissues of the lumen. Such stabilizing element may carry an imaging unit, and is preferably a balloon of a fixed or varying diameter. Thus, in some embodiments of the invention, the stabilizing element creates and stabilizes (maintains) an imaging working space within a body lumen, typically, maintaining the imaging unit on or in the vicinity of the central axis of the inspected lumen, with the field of view centralized at the central axis.

With regard to the stabilizing element, it should be noted that a distance between the stabilizing element and the inflatable balloon is fixed and is appropriately selected to ensure a desired maneuverability through lumen bends, as well as stability, and preferably centralization of the imaging unit. The distance should generally be desirably small, while taking into account the following: If such distance is too small it decreases the maneuverability, and if it is too large it decreases the stability and the centralization of the imaging unit (i.e. parallel arrangement of the central axis of the balloon with respect to the lumen axis.

In some embodiments, the balloon is made of low compliance material, i.e. a material which is substantially inelastic in a range of predetermined pressures (e.g. between 10 to 60 milibars), such that a volume of said balloon is not substantially changed by elastic deformation when the balloon is inflated. This is because high compliance may cause the balloon to elongate relatively more than a non-compliant balloon, when deformed within the lumen. The larger the elongation, the better is the chance that the portion of the carrier within the balloon will settle diagonally inside the balloon, since the balloon will tend to assume a shape which will maximize its internal volume. Therefore, a reduced elongation is desired, in order to decrease the condition that leads to the diagonal settling of the carrier within the balloon. In order to achieve a desired level of low compliance, the inflatable section of the balloon may be made of stiff material and/or the inflatable section may be coated with a stiffening agent.

The carrier traverses the balloon via two openings of the balloon, and is fixed to the balloon in the vicinity of at least one opening. The carrier includes a fluid passageway for carrying an inflating fluid from a fluid source into the balloon, and has one or more openings for releasing the inflating fluid into the balloon. Typically, the balloon forms a sealing contact with the inner walls of the lumen. When the balloon enters the body lumen and is inflated within the body lumen such that a contact is created between its outer circumference and the inner walls of the body lumen, circumferential pressure from the lumen's wall deforms the balloon with respect to an undeformed state thereof (i.e., a state in which the inflated balloon is not subject to an outer pressure). The larger the difference between the undeformed diameter of the balloon and the inner diameter of the lumen, the larger will be the deformation of the balloon.

When the balloon is deformed, the balloon has a tendency to settle into a shape which maximizes the balloon's volume. The pressure applied by the walls of the lumen onto the balloon induces the change of the balloons' shape by causing an increase in the longitudinal dimension of the balloon (elongated state). The expansion of the longitudinal dimension of the balloon causes a stress on the portion of the carrier within the balloon. This stress applies a certain internal tension force within the balloon inducing the balloon to turn such that the carrier settles diagonally intended to compensate for the internal tension. This destroys the orientation of the carrier with respect to the lumen axis.

The present invention solves the above problem by adding a degree of freedom in coupling between the balloon and the carrier in at least one of two coupling locations. The degree of freedom may be achieved by various configurations, using a sleeve member, slidable or not, at said at least one of the coupling locations, such that increase of the longitudinal dimension of the elongated-state balloon causes either sliding movement of the fixed-size sleeve along the carrier or decrease in the longitudinal dimension of the sleeve (e.g. by collapse).

An aspect of the present invention aims at maintaining the section of the carrier within the balloon near and substantially parallel to the main axis of the lumen. The apparatus of the invention thus includes a balloon, a carrier passing through the balloon along its axis and defining two coupling regions, and at least one sleeve associated with at least one of said two coupling regions. The balloon is made of substantially low compliance material, as described above. The sleeve is rigidly mounted to the balloon, and may be rigidly mounted on the carrier while including a foldable (collapsible) portion located between the inflatable balloon and the rigid mount of the carrier (location along the carrier to which the sleeve is fixed at its one end. The foldable portion is collapsible upon deformation of the inflatable balloon. Alternatively, the sleeve is rigidly coupled to the balloon but at its other end is slidably mounted on the carrier.

When the geometric constraint of the lumen deforms the balloon, r, the foldable portions of the sleeve fold along the carrier, constraining the horizontal deformation of the inflatable section to take place along the carrier, and decreasing pressure on the proximal and distal edges of the balloon. In this manner, the balloon is compelled to assume a shape different than the volume-maximizing shape described above. This new shape roughly resembles a cylinder, each end of which is capped by two half spheres having diameters about equal to half the diameter of the lumen. The proximal end of the portion of the carrier inside the balloon is pressed between the two proximal half-spheres, and the distal end of the portion of the carrier inside the balloon is pressed between the two proximal half-spheres. In this manner, the portion of the carrier inside the balloon is maintained in proximity to and substantially parallel to the main axis of the lumen.

Thus, according to a broad aspect of the invention, there is provided an apparatus for use with a biologically-compatible-fluid pressure source, comprising:

an elongated carrier comprising a fluid passageway, said carrier being adapted to be inserted through a proximal opening of a body lumen having a main axis and certain diameter;

an inflatable balloon assembly having an inflatable part self-deformable between its substantially circular geometric state and multiple elongated geometry states in which cross sectional dimensions of the inflatable balloon part are different in accordance with the diameter of the lumen, and being in fluid communication with said fluid passageway, the cross sectional dimension of the substantially circular geometric state being equal to or greater than said diameter of said body lumen; and at least one sleeve extending from at least one end respectively of said inflatable part of the balloon assembly along a central axis of said inflatable balloon part, said at least one sleeve being by its one end is rigidly coupled to the respective end of the balloon part and having one of the following configurations: (a) being by its other end fixed to the carrier at a certain location and being foldable and extendable in accordance with longitudinal deformation of the inflatable balloon part, and (b) having a fixed length and being by its other end slidable along the carrier in accordance with longitudinal deformation of the inflatable balloon part;

said carrier being configured to pass through said balloon and through said at least one sleeve, deformation of the inflatable part of the balloon maintaining the balloon assembly orientation such that said carrier passing through the balloon assembly substantially coincides with said main axis of said lumen.

The apparatus preferably comprises a stabilizer element mounted on said carrier at a certain fixed distance from the inflatable balloon assembly. The stabilizer may element may carry an imaging unit. Preferably the stabilizer element comprises a balloon.

Generally, the apparatus may include two sleeves, each configured as described above, which are located at opposites ends of the inflatable balloon assembly and extend along the respective segments of the carrier.

The inflatable part of the balloon assembly is made of one or more low compliance materials such that the balloon is substantially not extendable in response to a range of predetermined pressures, thus enabling said deformations.

In some embodiments, the sleeve, in its configuration where it is by its other end fixed to the carrier at the certain location and foldable and extendable in accordance with deformation of the inflatable balloon part, has a bellow shape.

The carrier is in fluid communications with a fluid source. That portion of the carrier, which passes through the balloon assembly, is formed with one or more apertures configured for releasing the pressurized fluid into the inflatable part of the balloon assembly.

As indicated above, the apparatus may comprise an imaging unit mounted on said carrier (e.g. on the stabilizing element). The apparatus is configured such that the deformation of the inflatable part of the balloon assembly maintains orientation of a field of view of the imaging unit (e.g. centralized with the main axis of the lumen).

In some implementations, the inflatable balloon assembly is configured and operable as a piston head providing a pressure seal between walls of the lumen and the balloon.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
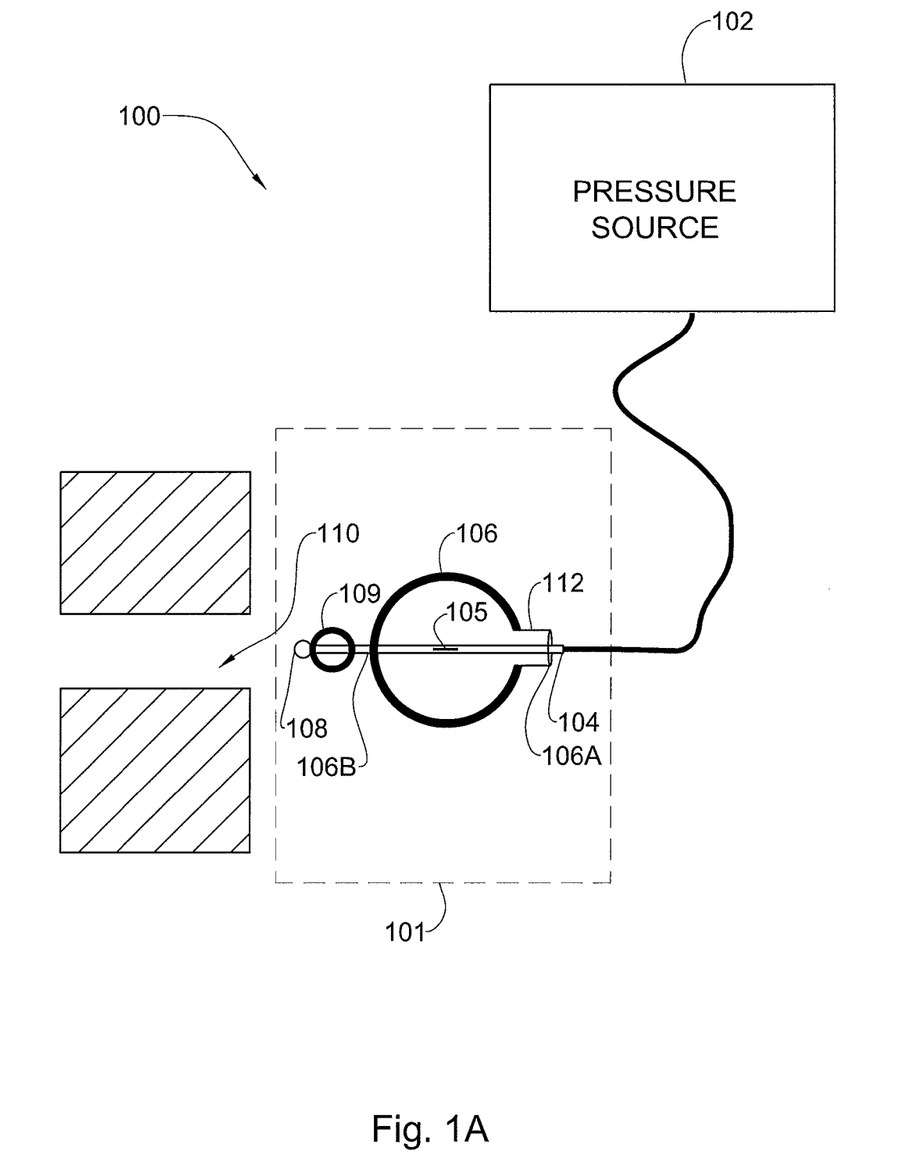
FIGS. 1A-1C are schematic drawings illustrating a system for examining a lumen of a body outside the body lumen (FIGS. 1A-1B) and within the body lumen (FIG. 1C) when a force is applied on the balloon from the walls of the lumen deforming the balloon towards its elongated, elliptical-like, shape.

Referring to the figures, FIG. 1A is a schematic drawing illustrating a system 100 utilizing an apparatus 101 of the present invention for examining a lumen of a body. The system 100 includes a biologically-compatible-fluid ($CO_2$ or similar) pressure source 102 configured to be connected to the apparatus 101, and an imaging device 108 which constitutes a medical device used in the apparatus 101. The apparatus 101 comprises a carrier 104 (typically, a bendable carrier) having an appropriate inlet (not shown) to be in fluid communication with the pressure source 102, and an inflatable balloon 106 mounted on the carrier, such that a portion of the carrier 104 traverses the balloon 106. Also provided in the apparatus is a stabilizing element 109 located at a distal portion of the carrier. In the present example, the stabilizing element 109 carries an imaging device 108 or an optical head thereof for enabling visual inspection of a lumen 110 in a subject.

The carrier 104 defines a fluid passageway for passing an inflating fluid from the fluid source 102 into the balloon 106. A portion of the carrier passing through the balloon 106 may be formed with one or more apertures 105 configured for releasing the pressurized fluid into the inflatable part of the balloon 106. A section of the carrier passing through the balloon 106 has one or more openings for releasing the inflating fluid into the balloon, in order to controllably inflate the balloon 106. It should be noted, although not specifically shown, that the system 100 also includes a control unit preprogrammed to control the pressure inside and outside the balloon to provide desired inflation of the balloon and a desired pressure on the rear of the balloon. As further shown in FIG. 1A, the relative accommodation of the carrier and the balloon defines two coupling regions between them 106A and 106B. The apparatus 101 includes at least one sleeve like member 112 at the at least one of the coupling regions respectively—single such sleeve 112 being shown in the present example.

Because a seal has to be created between the balloon and the inner walls of the body lumen, the balloon has an outer diameter that is slightly larger than (or equal to) the diameter of the lumen 110. Before the insertion of the balloon within the body lumen, when no constraint is applied on the outer surface of the balloon 106, the balloon 106 is in an inflated and undeformed (or circular) state. When the balloon 106 enters the body lumen 110 and is inflated within the body lumen, circumferential constraint of the lumen's wall deforms the balloon 106 towards a deformed, elongated state thereof. As will be described further below, the longitudinal deformation of the balloon is allowed due to a change in the condition of the sleeve (longitudinal dimension or position along the carrier), thereby maintaining the correct orientation of the balloon irrespective of its state, i.e. such orientation that the portion of the carrier passing through the balloon substantially coincides with the lumen axis.

Figure 1B:
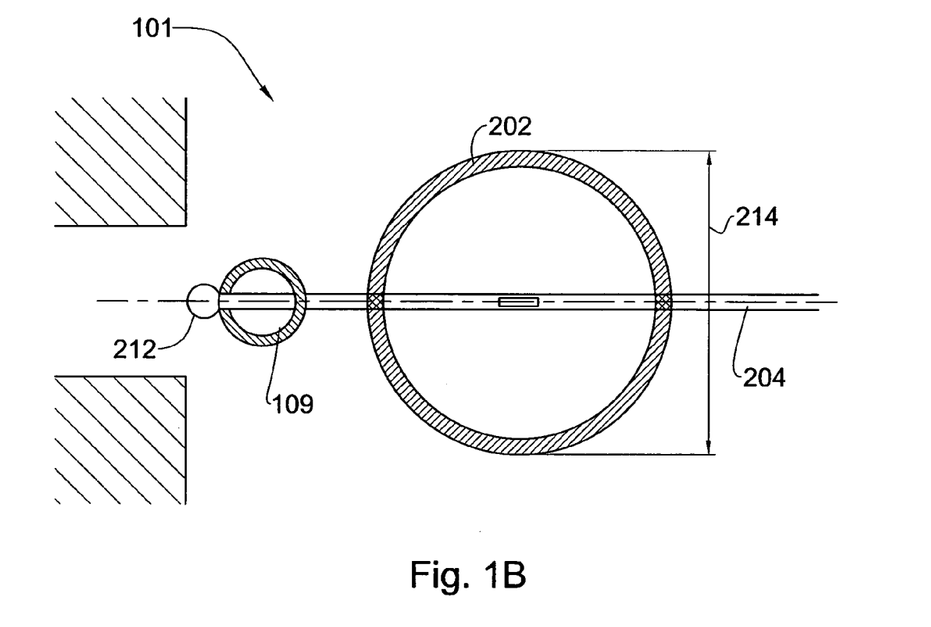
Figure 1C:
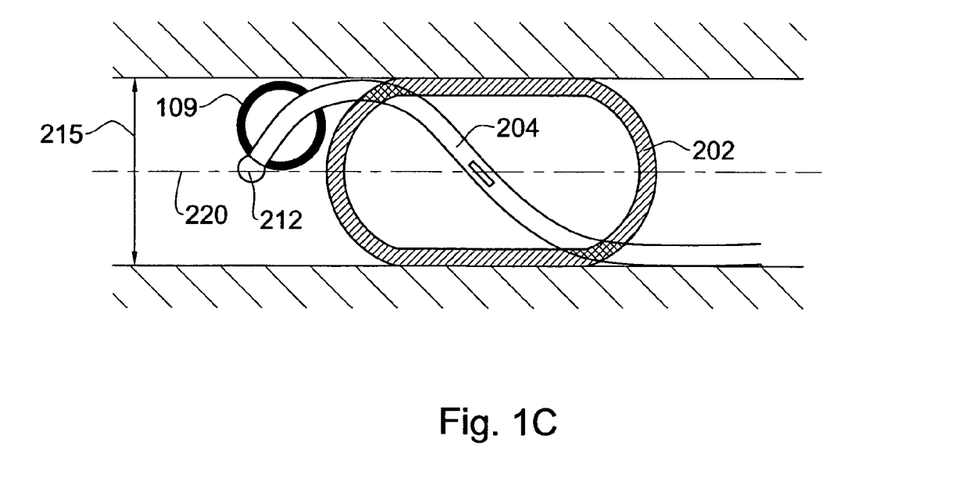

Reference is now made to FIGS. 1B and 1C illustrating the problems solved by the present invention. The figures are schematic drawings illustrating conventional coupling between a balloon and a carrier in an apparatus of the kind specified. In FIG. 1b, the balloon is in an undeformed state thereof, and in FIG. 1c the balloon is deformed due to circumferential constraint of a lumen wall.

It should be understood that generally, when inflating a balloon assembly inside a tube (e.g. lumen) having a smaller diameter than the balloon's original diameter (diameter of the balloon at maximal volume), the tendency of the balloon is to settle in a position that maximizes the volume inside the balloon. This position causes the carrier 204 to settle diagonally relative to the central axis of the tube 220.

As shown in FIG. 1b, the balloon 202 in an undeformed state thereof is spherical and has a diameter D (214). The balloon's diameter 214 is larger than the diameter $D_L$ (215) of the lumen. The balloon is intended to travel through the tube.

As seen on FIG. 1c, the deformed shape assumed by the balloon 202 in the lumen may be roughly described as an elliptical-like one (or modified ellipse). The elliptically shaped balloon has a cross sectional dimension equal to the diameter 215 of the lumen. The length of the elongated balloon 218 is herein defined as $L_1$. As the balloon 202 sports low compliance, a circumference thereof is substantially equal to that of the circular-shaped balloon, and therefore the compression of the balloon 202 (along a traverse (vertical) direction) results in a corresponding elongation along the tube (in a longitudinal direction). This causes the balloon 202 to tilt with respect to the central axis 220 of the lumen, which in turn results the section of the carrier 204 within the balloon 202 to be tilted accordingly, causing the distal portion of the carrier 204 to move towards the wall 216 of the lumen. If an imaging device 212 or an optical head thereof is joined to the distal tip of the carrier 204, such movement of the imaging device results in a change in the orientation of the FOV thereof with respect to the lumen, significantly reducing the FOV. It is thus evident that such inflatable balloon with no stabilizer and adjustment of its inflation within the cavity (body lumen) does not allow appropriate inspection and navigation of a medical device through a cavity of varying diameter, as well as insertion of the balloon with a medical device into cavities of different diameters, as the case may be.

As described above, the balloon has a tendency to settle into a shape which maximizes the balloon's volume, and the shape of the deformed balloon 202 has a higher volume than the shape of the deformed balloon 302. This is shown mathematically, as follows.

Because the balloon is made of low compliance material, a circumference of the balloon is relatively not changed during deformation. Therefore, the circumference of upper half of the deformed shape of the balloon is equal to half of the circumference of the balloon in the undeformed state (i.e., a circle, when the balloon 302 is spherical). Assuming that the balloon is spherical, $$\frac{\pi D}{2} = L_2 + (L_2 - D) + \frac{\pi D_L}{2}$$

where $L_2$ is the length of the cylindrical portion of the deformed balloon.

For a typical case in which $D_L = D/3$:
$L_2 = 1.0236 D$

Figure 1D:
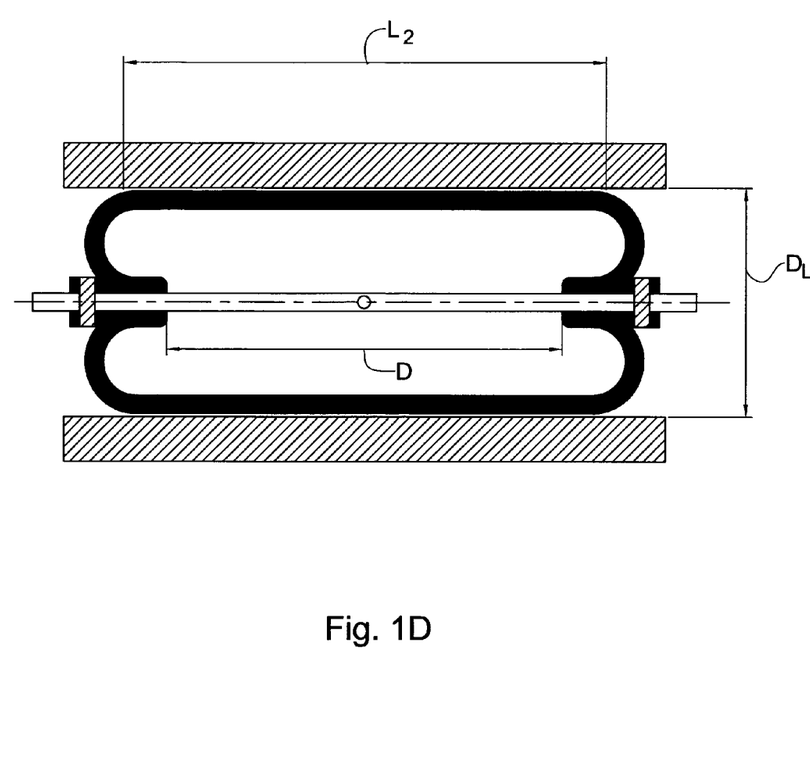
FIG. 1D shows an instable deformation of an inflatable balloon in the conventional balloon assembly.

Therefore the volume $V_2$ of the deformed balloon of FIG. 1D is:

$$V_2 = \frac{\pi}{4} D_L^2 L_2 + 2 \cdot \frac{\pi \left(\frac{D_L}{2}\right)^3}{6} = 0.09415 \, D^3$$

Referring now to FIG. 1C, the circumference of upper half of the deformed shape of the balloon is equal to half of the circumference of the balloon in the undeformed state (i.e., a circle, when the balloon is spherical).

$$\frac{\pi D}{2} = L_1 + \frac{\pi D_L}{2}$$

$$L_1 = 1.0472 \, D$$

The volume $V_2$ of the deformed balloon of FIG. 1C is $$V_1 = \frac{\pi}{4} D^2 L_1 + \frac{\pi D_L^3}{6} = 0.1108 \, D^3$$

From the above, it is seen that $V_1 > V_2$, thus when deformed, the balloon will tend to maximize its volume, by assuming the shape of FIG. 1C.

Figure 2A:
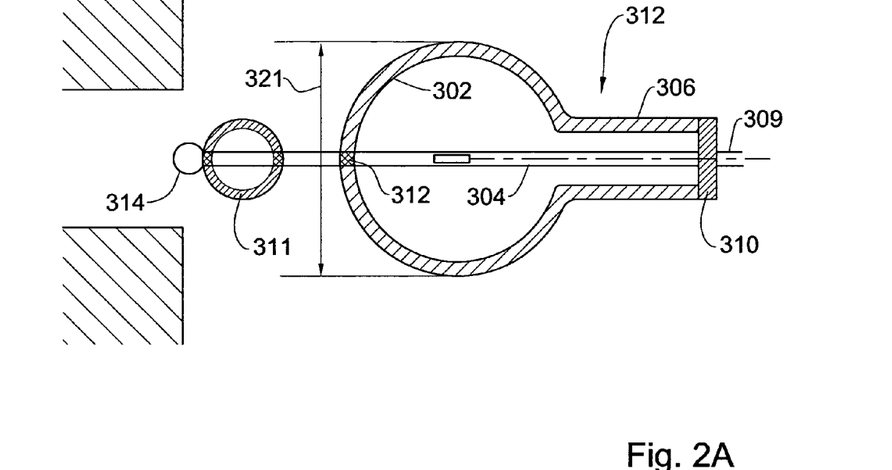
FIGS. 2a-2b are schematic drawings illustrating the system of the present invention including a foldable sleeve in an undeformed state (FIG. 2a) and in a deformed state due to circumferential constraint from a lumen wall (FIG. 2b)
Figure 2B:
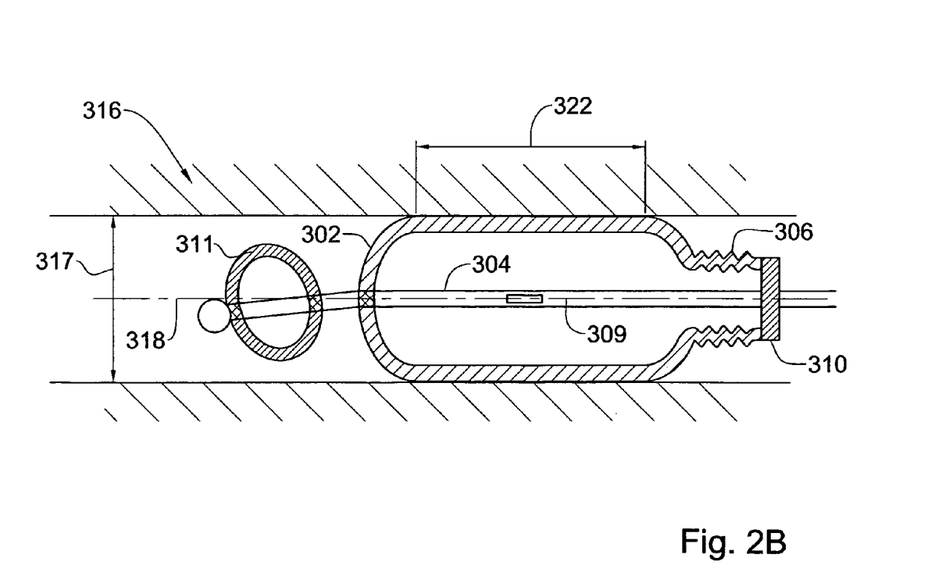

Reference is now made to FIGS. 2a-2b showing schematically more specific examples of an apparatus 300 of the present invention. the apparatus 300 comprises a balloon 302, a carrier 304, and a sleeve 306. In FIG. 2a, the balloon 302 is in an undeformed state thereof. In FIG. 2b, the balloon 302 is shifted into its deformed state due to circumferential constraint from a lumen wall. As shown, the configuration of the apparatus of the present invention provides that when in the deformed, elongated state of the balloon the section of the carrier within the balloon is maintained substantially coinciding with the main axis of the lumen 318.

When no constraint is applied to the balloon's outer surface, the balloon 302 has a diameter 321. The balloon's diameter 321 is larger than the diameter $D_L$ 317 of the lumen the balloon is intended to travel through, as mentioned above. The sleeve 306 is located at a coupling region 312 between the balloon and the carrier. In this specific example, the sleeve by itself defines the coupling region. The sleeve 306 is located between an inflatable part of the balloon and a fixed location 310 on the carrier. In other words, the sleeve is a part of the balloon assembly and is by its one end integral with the inflated part of the balloon and by the other end connected to the carrier. The carrier 304 passes through the sleeve 306 and through the inflated part of the balloon. The carrier 304 is fixed (rigidly mounted) to the sleeve 306 at the location 310, and to the balloon at the location 312. The sleeve 306 is configured to be foldable or collapsible along the carrier. This may be achieved by providing an appropriate length of the flexible sleeve material (capable of being shifted between its extended and collapsed, e.g. bellow states, or by providing an appropriate elasticity of the sleeve material. A stabilizer element 311 spaced from the inflated part of the balloon a certain desirably small distance and fixed to the carrier applies stability to the balloon being deformed.

The apparatus 300 is generally inserted into a lumen in a deflated state, and inflated to a pressure selected for ensuring that the balloon 302 comes into contact with the lumen wall 316 and provides a contact seal as described above. The selected pressure is usually a few dozen millibars.

When the constraint is applied by the lumen's wall 316 on the balloon 302, the foldable sleeve 306 folds gradually along the carrier 304 and allows the balloon 302 to assume a deformed shape to compensate for the elongation of the balloon being deformed. More specifically, the foldable sleeve 306 folds along the carrier 304, constraining the longitudinal deformation of the inflatable part of the balloon to take place along the carrier, and decreasing pressure on the proximal and distal edges of the balloon 302.

As shown in FIG. 2b, the longitudinal axis 309 of the elongated-shape balloon 302 is maintained substantially coinciding with the main axis 318 of the lumen.

In some embodiments, the apparatus 300 comprises an imaging unit 314 (or an optical head) carried by the stabilizing element 311. Although deformation of the balloon into an elongated state might cause a slight tilt of the stabilizing element with respect to the central axis of the lumen, the FOV of the imaging unit is still substantially centralized with the lumen axis. By using the apparatus of the present invention, the walls of the lumen within the panoramic FOV are nearly equidistant from the imaging unit, reducing the required depth of field and simplifying exposure.

Figure 3A:
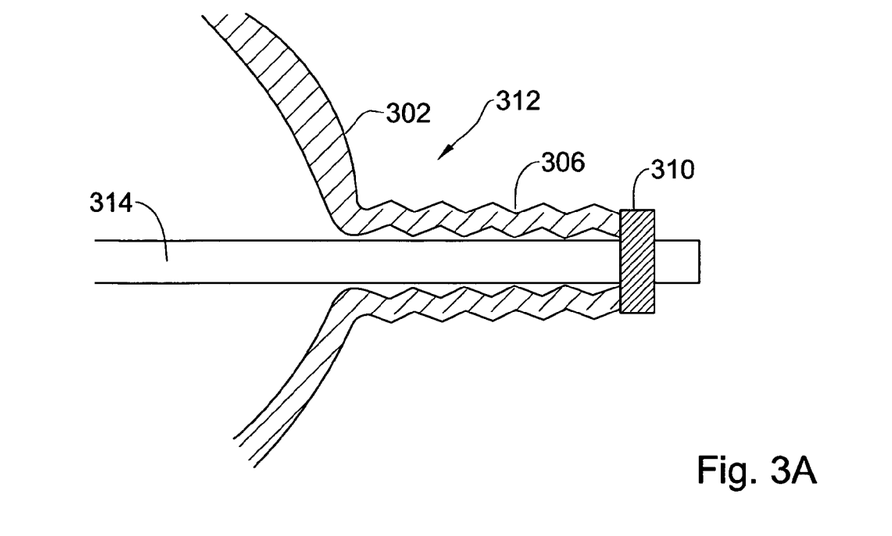
FIGS. 3a-3b are schematic enlarged illustrations of one possible configuration of a foldable sleeve and a carrier passing through the balloon. In particular, in FIG. 3a, the balloon is in an undeformed state thereof, and in FIG. 3b, the balloon is deformed due to circumferential constraint from a lumen wall.
Figure 3B:
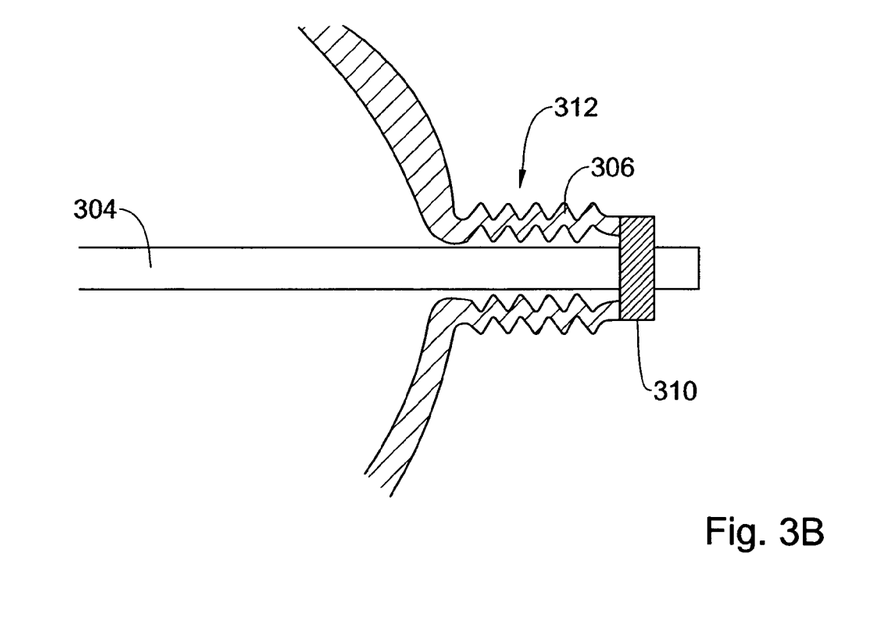

Reference is made to FIGS. 3a and 3b schematically showing (in an enlarged view) a possible configuration of the sleeve 306 in different states of the apparatus of FIGS. 2a-2b. In FIG. 3a, the balloon is undeformed and the sleeve is substantially extended over the carrier. In FIG. 3b, the deformation of the balloon causes the sleeve to fold upon itself. Because the sleeve 306 is foldable, the longitudinal extension of the balloon causes the sleeve 306 to fold upon itself, and this movement being assisted by the presence of the stabilizing element gives rise to the carrier-centering shape illustrated in FIG. 2b.

According to some embodiments of the present invention, the internal pressure within the balloon 302 is regulated in order to provide a pressure seal between a portion of the lumen on a proximal side of the balloon 302 and a portion of the lumen on a distal side of the balloon 302. This pressure seal enables a user to propel the apparatus 300 by applying a pressure onto the proximal side of the balloon 300, using the balloon 302 as a piston head.

The balloon may be made, for example, of Estene material or Estene-containing material composition e.g. including Estene 58277. The balloon material may have a thickness from a few microns to a few tens of microns. The sleeve 306 is rigidly mounted to the carrier, for example via an adapter, or may be tied via a suitable restraining unit.

Figure 4A:
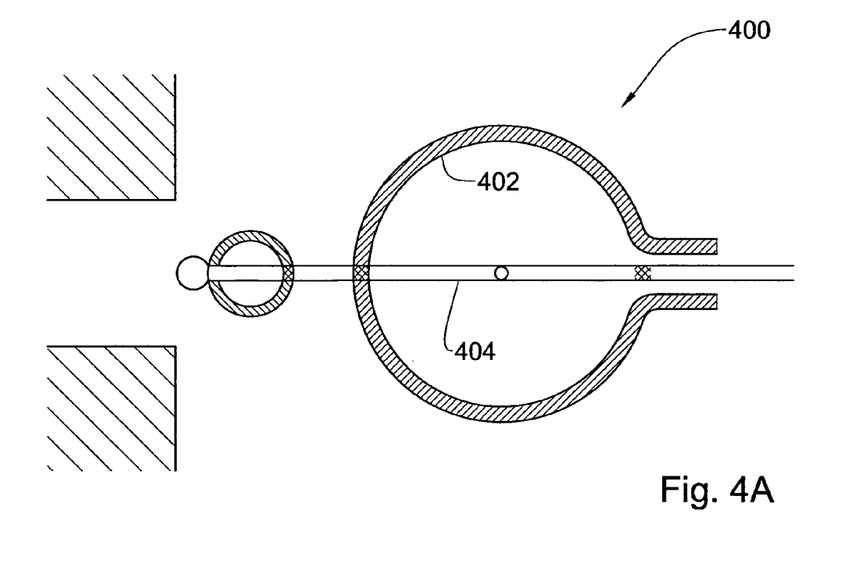
FIGS. 4a-4b are schematic drawings illustrating another possible configuration of the apparatus of the present invention, including a sliding sleeve mounted on the carrier. In particular, in FIG. 4a, the balloon is undeformed, and in FIG. 4b, the deformation of the balloon causes the sleeve to slide in a proximal direction along the carrier.
Figure 4B:
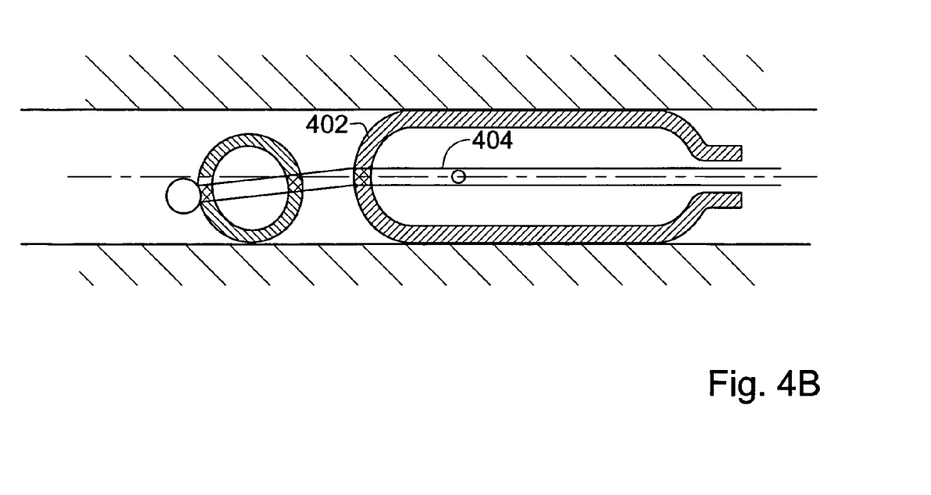

In some other embodiments of the invention, a sleeve is by its one end coupled to the balloon at the coupling region between the balloon and the carrier and by its other end is allowed for sliding movement along the carrier. Thus, in distinction to the previously described examples where the sleeve is fixed to the carrier but is extendable/collapsible in its length, here the sleeve has a fixed length by a changeable position along the carrier. This is schematically exemplified in FIGS. 4a and 4b, which similar to the above-described examples show respectively undeformed circular shaped balloon and deformed elongated balloon 402. As shown in the figures the sleeve 406 has a certain fixed length, while elongation of the balloon 402 causes its free end to slide along the carrier 404. It should be understood although not specifically shown that the movement of the sleeve along the carrier might be limited by proving a stopper member on the carrier.

Thus, the present invention provides a simple and effective solution for navigating a medical tool along body lumens. Those skilled in the art will readily appreciate that various modifications and changes can be applied to the embodiments of the invention as hereinbefore described without departing from its scope defined in and by the appended claims.

The invention claimed is:

1. An apparatus for use with a biologically-compatible-fluid pressure source, comprising:

an elongated carrier comprising a fluid passageway, said carrier being adapted to be inserted through a proximal opening of a body lumen having a main axis and diameter;

an inflatable balloon assembly having an inflatable part self-deformable between its substantially circular geometric state and multiple elongated geometry states in which cross sectional dimensions of the inflatable balloon part are varied in accordance with the diameter of the lumen, and being in fluid communication with said fluid passageway, the cross sectional dimension of the substantially circular geometric state being equal to or greater than said diameter of said body lumen; and at least one sleeve extending from at least one end respectively of said inflatable part of the balloon assembly along a central axis of said inflatable balloon part, said at least one sleeve being at its one end rigidly coupled to the respective end of the balloon part and having one of the following configurations: (a) being a part of the balloon assembly with its one end integral with the inflatable part of the balloon and with its other end fixed to the carrier at a determined location and being foldable and extendable in accordance with longitudinal deformation of the inflatable balloon part, or (b) having a fixed length and being by its other end slidable along the carrier in accordance with longitudinal deformation of the inflatable balloon part;

said carrier being configured to pass through said balloon via two openings of the balloon, and through said at least one sleeve, said carrier being fixed to the balloon in the vicinity of at least one opening, deformation of the inflatable part of the balloon maintaining the balloon assembly orientation such that said carrier passing through the balloon assembly substantially coincides with said main axis of said lumen.

2. The apparatus of claim 1, comprising a stabilizer element mounted on said carrier at a certain fixed distance from the inflatable balloon assembly.

3. The apparatus of claim 2, comprising an imaging unit mounted on said stabilizing element, the deformation of the inflatable part of the balloon assembly maintaining orientation of a field of view of the imaging unit.

4. The apparatus of claim 2, wherein the stabilizing element comprises a balloon.

5. The apparatus of claim 4, comprising an imaging unit mounted on said stabilizing element, the deformation of the inflatable part of the inflatable balloon assembly maintaining orientation of a field of view of the imaging unit.

6. The apparatus of claim 1, wherein said inflatable part of the balloon assembly is made of one or more low compliance materials such that the balloon is substantially not extendable in response to a range of predetermined pressures, thus enabling said deformations.

7. The apparatus of claim 1, wherein said at least one sleeve, in its configuration with its other end fixed to the carrier at the determined location and foldable and extendable in accordance with deformation of the inflatable balloon part, has a bellow shape.

8. The apparatus of claim 7, wherein said inflatable part of the balloon assembly is made of one or more low compliance materials such that the balloon is substantially not extendable in response to a range of predetermined pressures, thus enabling said deformations.

9. The apparatus of claim 1, wherein said carrier is in fluid communication with a fluid source and a portion of the carrier passing through the balloon assembly is formed with one or more apertures configured for releasing the pressurized fluid into said inflatable part of the balloon assembly.

10. The apparatus of claim 1, comprising an imaging unit mounted on said carrier, the deformation of the inflatable part of the balloon assembly maintaining orientation of a field of view of the imaging unit.

11. The apparatus of claim 10, wherein said at least one sleeve, in its configuration with its other end fixed to the carrier at the determined location and foldable and extendable in accordance with deformation of the inflatable balloon part, has a bellow shape.

12. The apparatus of claim 11, said inflatable part of the balloon assembly is made of one or more low compliance materials such that the balloon is substantially not extendable in response to a range of predetermined pressures, thus enabling said deformations.

13. The apparatus of claim 1, wherein said inflatable balloon assembly is configured and operable as a piston head providing a contact seal between walls of the lumen and the balloon.

14. The apparatus of claim 13, wherein said inflatable part of the balloon assembly is made of one or more low compliance materials such that the balloon is substantially not extendable in response to a range of predetermined pressures, thus enabling said deformations.

15. The apparatus of claim 14, wherein said at least one sleeve, in its configuration being by its other end fixed to the carrier at the certain location and foldable and extendable in accordance with deformation of the inflatable balloon part, has a bellow shape.

16. The apparatus of claim 15, comprising an imaging unit mounted on said carrier, the deformation of the inflatable part of the balloon assembly maintaining orientation of a field of view of the imaging unit.

17. The apparatus of claim 15, comprising a stabilizer element mounted on said carrier at a certain fixed distance from the inflatable balloon assembly.

18. The apparatus of claim 17, comprising an imaging unit mounted on said stabilizing element, the deformation of the inflatable part of the balloon assembly maintaining orientation of a field of view of the imaging unit.

* * * * *

UNITED STATES PATENT AND TRADEMARK OFFICE
CERTIFICATE OF CORRECTION

PATENT NO. : 8,939,895 B2
APPLICATION NO. : 13/510194
DATED : January 27, 2015
INVENTOR(S) : Tal Simchony et al.

Page 1 of 1

It is certified that error appears in the above-identified patent and that said Letters Patent is hereby corrected as shown below:

In the Claims:

At column 10, claim number 2, line number 49, please change "a certain fixed" to --a fixed--.

Signed and Sealed this
Twenty-eighth Day of April, 2015

Michelle K. Lee
*Director of the United States Patent and Trademark Office*